United States Patent [19]

Vecsei et al.

[11] Patent Number: 4,938,771
[45] Date of Patent: Jul. 3, 1990

[54] FEMORAL PORTION OF A HIP JOINT PROSTHESIS

[76] Inventors: Vilmos Vecsei; Karl Obersteiner, both of 235 E. 42nd St., New York, N.Y. 10017

[21] Appl. No.: 244,448

[22] Filed: Sep. 15, 1988

[30] Foreign Application Priority Data

Sep. 17, 1987 [DE] Fed. Rep. of Germany ... 8712578[U]

[51] Int. Cl.$^5$ ............................................. A61F 2/32
[52] U.S. Cl. .......................................... 623/23; 623/16
[58] Field of Search ....................... 623/16, 18, 19, 20, 623/22, 23

[56] References Cited

U.S. PATENT DOCUMENTS

| | | | |
|---|---|---|---|
| 4,146,936 | 4/1979 | Aoyagi et al. | 623/23 |
| 4,266,302 | 5/1981 | Tornier et al. | 623/22 |
| 4,459,708 | 7/1984 | Buttazzoni | 623/23 |
| 4,530,114 | 7/1985 | Tepic | 623/23 |
| 4,650,489 | 3/1987 | Thompson | 623/16 |
| 4,657,552 | 4/1987 | Karpf | 623/23 |
| 4,738,681 | 4/1988 | Koeneman et al. | 623/23 |
| 4,743,263 | 5/1988 | Petrtyl et al. | 623/23 |
| 4,750,905 | 6/1988 | Koeneman et al. | 623/16 |

FOREIGN PATENT DOCUMENTS

| | | |
|---|---|---|
| 0245846 | 11/1987 | European Pat. Off. . |
| 3028393 | 2/1982 | Fed. Rep. of Germany . |
| 3247726 | 12/1982 | Fed. Rep. of Germany . |

OTHER PUBLICATIONS

Bombelli et al; "Early Results of the RM–isoelastic Cementless Total Hip Prosthesis: 300 Consecutive Cases with 2-Year Follow-Up"; American Hip Society Symposium (1984).

Primary Examiner—David J. Isabella
Attorney, Agent, or Firm—Vidas & Arrett

[57] ABSTRACT

A femoral portion of a hip joint prosthesis comprises a shank portion which merges into an angled neck portion optionally via a collar, with the neck portion being connected or adapted to be connected to a joint ball. The upper or proximal portion of the shank is defined by a framework structure such that the distribution of the tension and thrust forces approximates the force distribution in the natural bone.

8 Claims, 2 Drawing Sheets

FEMORAL PORTION OF A HIP JOINT PROSTHESIS

BACKGROUND OF THE INVENTION

The invention is directed to a femoral portion of a hip joint prosthesis.

As is known, femoral shank prostheses are used to replace the inoperable proximal femur, particularly the femur head. During implantation the femur head and femur neck are surgically removed, and the prosthesis shank is driven into the free-drilled femoral canal. The shank is either secured in the femoral canal by bone cement or retained solely by a positive connection (cementless prosthesis). In the latter case the prosthesis shank is relatively elongated and provided with surface irregularities, holes or the like in order to allow an ingrowth of the bone.

Two complications may occur in connection with the femoral portions of the hip joint prosthesis which cannot be completely mastered. The load in the proximal portion of a femur is a tension-thrust-load. In the lateral portion above all a tension load occurs while in the medial portion a thrust-load is prevailing. Since the shank prosthesis is approximated the shape of the proximal femur the prosthesis is loaded in a similar manner. Endoprostheses normally consist of a metal or a metal alloy compatible to the body. The materials used for this purpose have an elasticity modul deviating from that of the natural bone which by the way has a very different interior structure in dependence from the load applied to. The normally occurring load is a so-called alternating load which causes continuously a relatively small work of deformation in the bone or the prosthesis, respectively. This work of deformation causes a loosening of the prosthesis above all in the transient range between the prosthesis and the adjacent bone surface whereby the hip joint prosthesis becomes unoperable and occasionally must be removed. A loosening is occurring also if bone cement is used. The bone cement is fixedly connected with the bone while the loosening occurs between the cement and the prosthesis or between the cement and the bone, respectively, or between both. The re-implantation of hip joint prostheses is a very complicated procedure which heavily stresses the patient.

If the shank prostheses are not forged or made of unsuitable alloy material this leads to fractures from time to time. Sometimes such breakages or fractures rely on prosthesis portions not perfectly cast, the prosthesis portions may contain tension cracks or shrinking holes or the like. This phenomenon, however, is relatively seldom. Rather, it has been stated that also completely operable prosthesis shanks may fracture if they are implanted over a longer time period. In these cases so-called fatigue fractures happen.

SUMMARY OF THE INVENTION

An object of the invention is to provide a femoral portion of a hip joint prosthesis which approximately behaves as the natural bone in view of the loadability and which can be completely incorporated by the bone.

This problem is solved by the features of the present invention.

With the invention it has been recognized that with a massive form of the shank it is not possible to structure the shank such that it provides a similar elasticity behavior as a natural bone. Therefore the invention provides a framework-like shape of the shank in the upper or proximal portion thereof. The lower shank portion can be made massive since normally it is uncritical as to the occurrancy of fractures; on the other hand it plays a role for the primary fixation of the freshly implanted prosthesis.

A framework consisting of a plurality of bars or rods can be made sufficiently rigid that the occurring loads can be obviated as to the mount thereof so that a plastic deformation does not happen. It is decisive, however, that the strength and the amount or the location, respectively, of the rods are selected such that the strength behavior or the elasticity behavior, respectively, of the natural bone in the respective portions are simulated. Since the load distribution in the natural femur is known and also the physical structure thereof it is possible without more ado to calculate and dimension the framework by means of a computer so that the desired properties will be obtained.

The framework of the shank must be formed such that it fits the femur channel more or less and does not cause any inconvenience. Therefore, an embodiment of the invention provides that the outer contour in the framework portion is defined by longitudinal rods or bars extending in the longitudinal direction of the shank, the longitudinal rods being supported relative to each other by connection rods or bars. Preferably, the longitudinal rods are arranged such that the preferably rounded edges thereof define the lateral border surfaces of the shank. Front and rear sides of a shank normally are defined by parallel surfaces while the other oppositely located surfaces are arcuate in cross section. This contour is maintained by the longitudinal rods, a hollow space or cavity is left between the longitudinal rods. First connection rods may interconnect adjacent longitudinal rods. Their outer surfaces thus are in the same plane as the associated outer surfaces of the shank. Second connection rods may interconnect diagonal longitudinal rods or bars.

In order to prevent a notch effect the longitudinal bars radially merge into the massive distal portion of the shank. Therefore, according to a further embodiment of the invention groove-like depressions are formed in the outer surface of the shank in the massive portion thereof, the depressions progressively deepen from the outer surface of the shank towards the proximal end thereof, the depressions cause a gradual raising of the longitudinal bars from the massive shank portion on both sides of the depressions.

The prosthesis according to the invention as a matter of fact consists of a material compatible to body. Preferably, the prosthesis is cast. Also relatively complicated framework structures can be made by cast techniques. However, forging, sintering or combined processes can be used.

DETAILED DESCRIPTION OF THE INVENTION

The invention is explained herebelow along an example illustrated by drawings.

Figure 1:
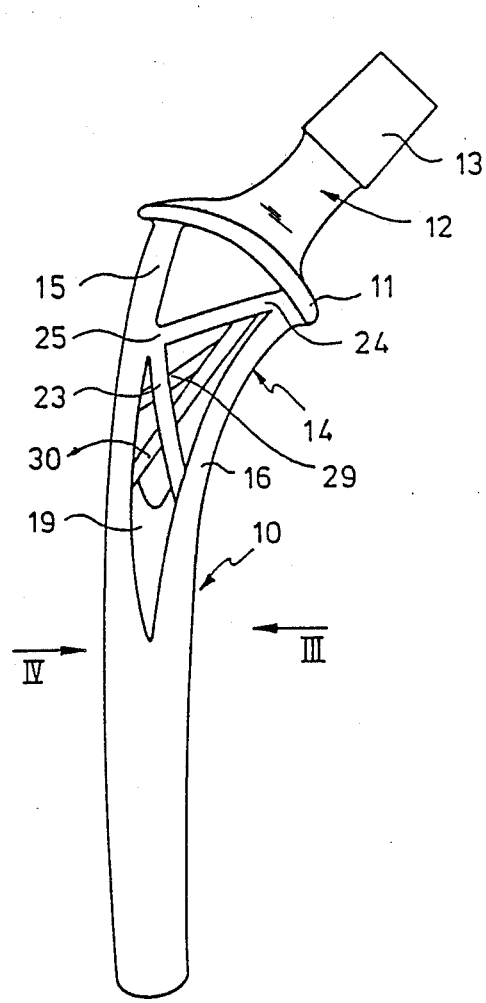
FIG. 1 shows the rear view of the endoprosthesis according to the invention.

Before the details in the drawings are explained it should be noted that each of the mentioned features per se or in connection with features of the claims are constituents of the invention.

The femoral portion of a hip joint endoprosthesis shown in the FIGS. 1 to 4 comprises a shank 10 which has a collar 11 at the proximal end thereof. The collar 11 slightly extends beyond the shaft in medial and lateral direction. A neck portion 12 joins to the collar, an external cone 13 being formed to the neck portion, the cone 13 being adapted to receive the internal cone of a joint ball.

Two thirds of the shank 10 if looked from the distal end upwardly are made of massive material in a conventional manner. The upper third is formed as framework 14. The framework 14 includes four longitudinal bars 15, 16, 17 and 18. The longitudinal bars 15 to 18 define the outer contour of the proximal portions of shank 10 and are located in the edge portions thereof between the four outer surfaces of shank 10. The external edges of the longitudinal bars 15 to 18 are rounded. Groove-like depressions 19, 20, 21, 22 are formed between adjacent bars 15 to 18, the depressions deepen and broaden gradually from the massive portion to the proximal end. They enable the gradual raising of the longitudinal bars 15 to 18 out of the massive portion of shank 10.

Figure 2:
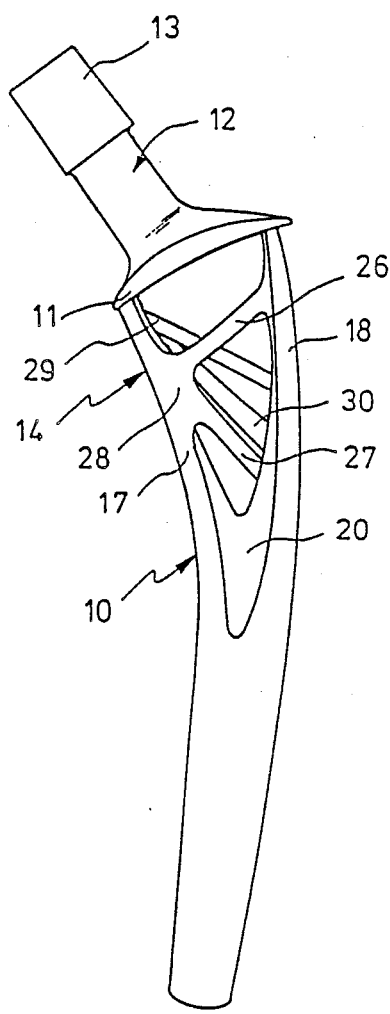
FIG. 2 shows the front view of the endoprosthesis according to FIG. 1.
Figure 3:
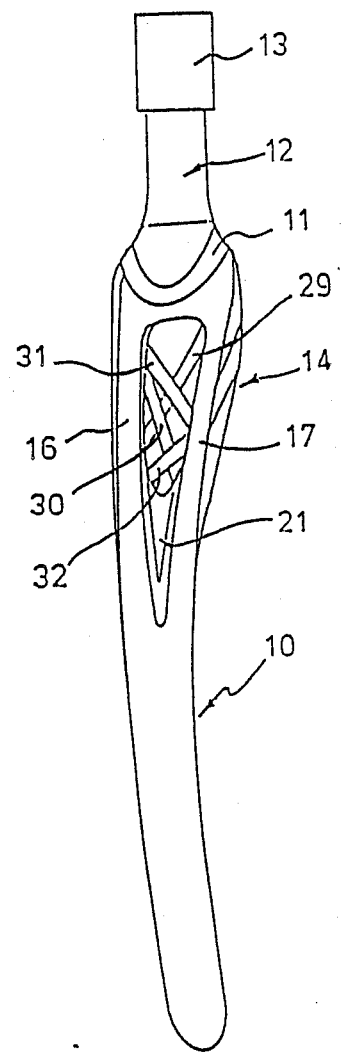
FIG. 3 shows the medial view of the endoprosthesis according to FIG. 1 if looked in direction of arrow 3.
Figure 4:
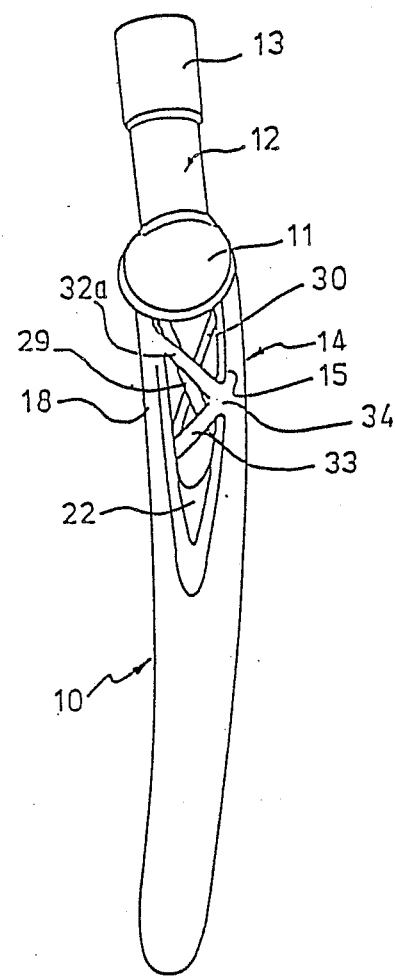
FIG. 4 shows the lateral view of the endoprosthesis of FIG. 1 if looked in the direction of arrow 4.

The longitudinal bars 15, 16 are interconnected by two connection bars 23 and 24. The connection bars 23, 24 are jointly connected to the longitudinal bar 15 at the mid height thereof as shown at 25, the connection bars defining approximately a right angle therebetween and extending to the ends of the longitudinal bar 16. The outer surfaces of the connection bars 23, 24 approximately lie at the same height as the outer surfaces of longitudinal bars 15, 16. Correspondingly the longitudinal bars 17, 18 are interconnected by two connection bars 26, 27. They extend from a common connection point 28 at the mid height of the longitudinal bar 17 to the end portions of longitudinal rod 18, defining approximately a right angle therebetween. The course or direction of the connection bars 23, 24 on one side and of 26, 27 on the other side is opposite. It is to be noted that the connection bars in FIGS. 1 and 2 are omitted for illustrative reasons on that shank which cannot be observed.

The longitudinal bars 15, 17 are interconnected through the diagonally extending second connection bar 29. The second connection bar 29 is connected to the longitudinal bar 15 somewhat below the connection point 25 and extends approximately to the upper end of the longitudinal bar 17. The longitudinal bars 16, 18 are interconnected by a diagonal second connection bar 30. It is connected to the lower portion of longitudinal bar 18 and extends to the upper end of longitudinal bar 16.

The longitudinal bars 16, 17 are interconnected by two connection bars 31, 32. They are connected to longitudinal bar 17 at the mid height thereof adjacent each other and extend to longitudinal bar 16 defining nearly a right angle. Correspondingly, the longitudinal bars 18, 15 are interconnected by two connection rods 32a, 33. They are connected to longitudinal bar 15 at 34 and extend to longitudinal bar 18 defining nearly a right angle.

The longitudinal bars have a considerable larger cross section than the connection bars. The number of connection rods, the cross section thereof and their spatial arrangement and the connection to the longitudinal bars is not restricted to the example shown in the FIGS. 1 to 4. They can be individually changed. Further it is possible to define the spatial arrangement of the framework and the cross sections by a calculation through a computer so that a distribution of load or the forces will be obtained corresponding to that of the natural bone.

The shown prosthesis preferably is implanted cementless whereby bone substance may ingrow into the framework in the interior of the prosthesis. This portion, further, could be filled with spongiosa during the surgical operation.

We claim:

1. A femoral component of a hip joint prosthesis comprising a shank, having a distal portion and a proximal portion which merges into a neck angulated with respect to the distal shank portion, the neck being adapted for connection a joint ball, and the proximal portion of the shank being defined by a structural framework, the contour of said framework being defined by four longitudinal bars spaced from each other and extending in substantially the longitudinal direction of the shank and arranged such that they define a proximal shank portion outer contour that is generally quadrilateral in transverse cross section with rounded edges, the longitudinal bars being supported relative to one another by a plurality of trusses extending between and through the hollow space between the longitudinal bars, the framework being configured such that the distribution of the tensile and compressive forces approximates the force distribution in the proximal portion of the natural femur.

2. A femoral component of claim 1 further comprising a transversely-extending collar joining the neck and proximal shank portion.

3. A femoral component of claim 1 formed as a unitary, single-piece cast article made of a biocompatible metallic material.

4. A femoral component of claim 1 wherein said framework is provided with a coating of a material which promotes the ingrowth of bone tissue.

5. A femoral component of claim 1 wherein said distal shank portion is made of massive material and wherein said longitudinal bars gradually merge into said massive distal shank portion.

6. A femoral component of a hip joint prosthesis comprising a shank, having a distal portion and a proximal portion which merges into a neck angulated with respect to the distal shank portion, the neck being adapted for connection to a joint ball, and the proximal portion of the shank being defined by a structural framework, the contour of said framework being defined by four longitudinal bars spaced from each other and extending in substantially the longitudinal direction of the shank and arranged such that they define a proximal shank portion outer contour that is generally quadrilateral in transverse cross section with rounded edges, the longitudinal bars being supported relative to one another by a plurality of trusses extending between and through the hollow space between the longitudinal bars, said trusses comprising a first set of trusses interconnecting adjacent pairs of longitudinal bars on said outer contour and the framework being configured such that the distribution of the tensile and compressive forces approximates the force distribution in the proximal portion of the natural femur.

7. A femoral component of claim 6 further comprising a second set of trusses interconnecting diagonally arranged pairs of longitudinal trusses on said outer contour, the bars of said second set crossing each other in the hollow inner space defined within the framework outer contour.

8. A femoral component of a hip joint prosthesis comprising a shank, having a massive distal portion and a proximal portion which merges into a neck angulated with respect to the distal shank portion, the neck being adapted for connection to a joint ball, and the proximal portion of the shank being defined by a structural framework, the contour of said framework being defined by four longitudinal bars spaced from each other and extending in substantially the longitudinal direction of the shank and arranged such that they define a proximal shank portion outer contour that is generally quadrilateral in transverse cross section with rounded edges, the longitudinal bars being supported relative to one another by a plurality of trusses extending between and through the hollow space between the longitudinal bars, said longitudinal bars gradually merge into said massive distal shank portion, the framework being configured such that the distribution of the tensile and compressive forces approximates the force distribution in the proximal portion of the natural femur and wherein four depressions are formed in the outer surface of said massive distal shank portion between adjacent longitudinal bars, which depressions deepen and broaden progressively towards the proximal direction such that said four longitudinal bars on the sides of the depressions gradually rise from the massive distal shank portion.

* * * * *